United States Patent
Splett et al.

(10) Patent No.: US 6,988,215 B2
(45) Date of Patent: Jan. 17, 2006

(54) METHOD AND APPARATUS FOR SYNCHRONIZATION OF CLOCK DOMAINS

(75) Inventors: Vincent E. Splett, Apple Valley, MN (US); Carl A. Schu, Plymouth, MN (US); Paul J. Huelskamp, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 757 days.

(21) Appl. No.: 09/952,914

(22) Filed: Sep. 14, 2001

(65) Prior Publication Data

US 2003/0056135 A1 Mar. 20, 2003

(51) Int. Cl.
*G06F 1/12* (2006.01)

(52) U.S. Cl. .......................... 713/400; 607/16
(58) Field of Classification Search ................. 713/400, 713/401, 322; 327/144, 145; 607/16
See application file for complete search history.

(56) References Cited

U.S. PATENT DOCUMENTS

| 5,022,395 A | | 6/1991 | Russie |
| 5,099,141 A | * | 3/1992 | Utsunomiya ................. 327/145 |
| 5,254,888 A | * | 10/1993 | Lee et al. .................... 327/298 |
| 5,533,032 A | | 7/1996 | Johnson |
| 5,654,988 A | * | 8/1997 | Heyward et al. ........... 327/144 |
| 5,721,886 A | * | 2/1998 | Miller ......................... 713/400 |
| 6,260,152 B1 | * | 7/2001 | Cole et al. .................. 713/400 |
| 6,799,280 B1 | * | 9/2004 | Edenfield et al. ........... 713/400 |
| 2002/0135408 A1 | * | 9/2002 | Chiu ........................... 327/145 |

FOREIGN PATENT DOCUMENTS

| EP | 0 032 818 A2 | * | 7/1981 |
| EP | 001113353 A2 | * | 7/2001 |

* cited by examiner

*Primary Examiner*—Fritz Fleming

(57) ABSTRACT

A method and an apparatus for synchronizing clock domains. A slow clock signal is received. A circuit in a slow clock domain is operated based upon the slow clock signal. A fast clock signal is received. The slow clock signal is synchronized using the fast clock signal. The operation of the circuit is modified from the slow clock domain to the fast clock domain, modifying the operation comprising changing a clock operation frequency during a non-transition period of the slow clock.

7 Claims, 12 Drawing Sheets

METHOD AND APPARATUS FOR SYNCHRONIZATION OF CLOCK DOMAINS

FIELD OF THE INVENTION

This invention relates generally to acquisition of physiological data, and, more particularly, to a method and apparatus for performing synchronization between clock domains.

DESCRIPTION OF THE RELATED ART

The technology explosion in the implantable medical devices industry has resulted in many new and innovative devices and methods for analyzing and improving the health of a patient. The class of implantable medical devices now includes pacemakers, implantable cardioverters, defibrillators, neural stimulators, and drug administering devices, among others. Today's state-of-the-art implantable medical devices are vastly more sophisticated and complex than early ones, capable of performing significantly more complex tasks. The therapeutic benefits of such devices have been well proven.

There are many implementations of implantable medical devices that provide data acquisition of important physiological data from a human body. Many implantable medical devices are used for cardiac monitoring and therapy. Often these devices comprise sensors that are placed in blood vessels and/or chambers of the heart. Often these devices are operatively coupled with implantable monitors and therapy delivery devices. For example, such cardiac systems include implantable heart monitors and therapy delivery devices, such as pacemakers, cardioverter, defibrillators, heart pumps, cardiomyostimulators, ischemia treatment devices, drug delivery devices, and other heart therapy devices. Most of these cardiac systems include electrodes for sensing and gain amplifiers for recording and/or driving sense event signals from the inter-cardiac or remote electrogram (EGM).

As the functional sophistication and complexity of implantable medical device systems have increased over the years, it has become increasingly useful to include a system for operation in a multi-mode fashion. Multi-mode operation may be used to conserve battery resources in the implantable medical device. Many body-implantable medical devices may receive operational power from an internal power source, such as a battery. The battery may serve a variety of functions, including, but not limited to, supplying power to electronic components of the device and charging capacitors that may discharge through electric leads into the heart to regulate heart rhythms. Conserving battery power is important, since replacing a battery from an implantable medical device can be invasive. Therefore, much effort has been devoted to increase conservation of battery resources.

Use of multi-mode operation may lead to more efficient use of battery power, however, switching between the multi-mode operations may cause malfunctions in the implantable medical device. Often, when switching operation-mode to another, certain errors, ringing, false signal rises, etc., may occur. Such errors can cause malfunction of a circuit, making the overall implantable medical system unpredictable at times. Errors occurring in implantable medical devices can cause harm to the health of a patient.

The present invention is directed to overcoming, or at least reducing the effects of, one or more of the problems set forth above.

SUMMARY OF THE INVENTION

In one aspect of the present invention, a method is provided for performing synchronization between clock domains. A slow clock signal is received. A circuit in a slow clock domain is operated based upon the slow clock signal. A fast clock signal is received. The slow clock signal is synchronized using the fast clock signal. The operation of the circuit is modified from the slow clock domain to the fast clock domain, modifying the operation comprising changing a clock operation frequency during a non-transition period of the slow clock.

In another aspect of the present invention, an apparatus is provided performing synchronization between clock domains. The apparatus of the present invention comprises: a processor; a control logic operatively coupled to the processor, the control logic to generate at least one control signal in response to a command from the processor; a data acquisition controller operatively coupled with the control logic, the data acquisition controller to acquire physiological data in response to an assertion of at least one control signal from the control logic; and a clock controller operatively coupled with the control logic, the clock controller to modify a operation clock from a slow clock domain to a fast clock domain by synchronizing the slow clock domain to the fast clock domain, the clock controller being capable of performing a operating clock transition during a non-transition period of the slow clock.

BRIEF DESCRIPTION OF THE DRAWINGS

The invention may be understood by reference to the following description taken in conjunction with the accompanying drawings, in which like reference numerals identify like elements, and in which.

Figure 1:
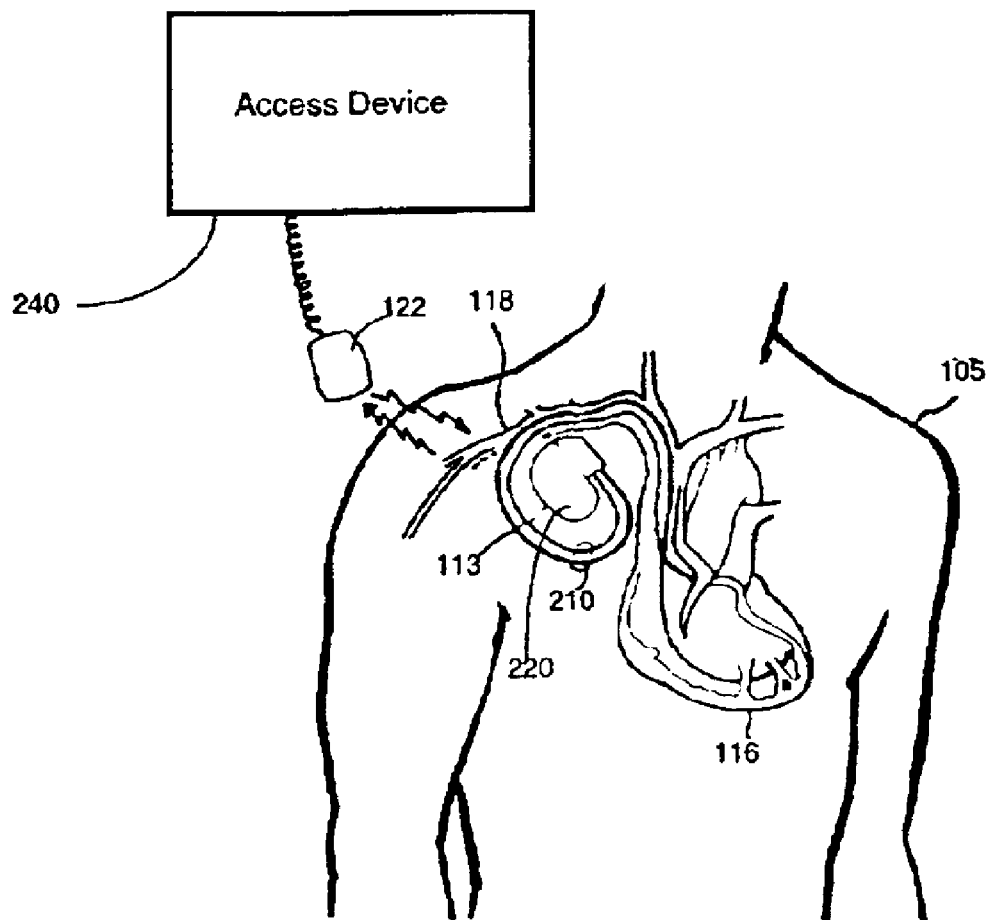
FIG. 1 is a simplified diagram of an implementation of an implantable medical device in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are many discrete processes involving collecting, storing, and presenting physiological trends of a patient, as well as in delivering therapies (e.g., a cardiac therapy). A battery located within an implantable medical device provides the power necessary for performing such operations. Therefore, conserving battery power can provide for longer, uninterrupted operation of the implantable medical device. Many systems utilize a sleep mode when a certain portion of a circuit in the implantable medical device is not immediately needed, in order to conserve power. Often, a different clock rate may be used for a sleep mode operation, whereas a faster clock rate may be used for normal operation that requires more robust circuit functions. For example, simple monitoring functions may be performed using a slower operation clock frequency while more complex circuitry in the implantable medical device may be used in a sleep mode. Upon detection of a cardiac event, a fast operation clock may be invoked in order to process acquired physiological data and deliver a cardiac therapy in response to the processing of the physiological data.

Often, when switching from one clock to another (e.g., switching from a slow clock to a fast clock), certain errors, ringing, false signal rises, etc., may occur. Such errors can cause malfunction of a circuit making the overall implantable medical system unreliable. Embodiments of the present invention provide for synchronizing clock signals during a transition from one clock-mode/domain to another.

FIG. 1 illustrates one embodiment of implementing an implantable medical device into a human body. A sensor 210 (e.g., leads) placed upon the heart 116 of the human body 105 is used to acquire and process physiological data. An implantable medical device 220 collects and processes a plurality of data acquired from the human body. In one embodiment, the implantable medical device 220 may be a pacemaker or a defibrillator. The data acquired by the implantable medical device 220 can be monitored by an external system, such as the access device 240 comprising a programming head 122, which remotely communicates with the implantable medical device 220. The programming head 122 is utilized in accordance with medical device programming systems known those skilled in the art having the benefit of the present disclosure, for facilitating two-way communications between the pacemaker 220 and the access device 240.

In one embodiment, a plurality of access devices 240 can be employed to collect a plurality of data processed by the implantable medical device 220 in accordance with embodiments of the present invention. The implantable medical device 220 is housed within a hermetically sealed, biologically inert outer canister or housing 113, which may itself be conductive so as to serve as an electrode in the pacemaker's pacing/sensing circuit. One or more pacemaker sensors/therapy-delivery devices (leads), collectively identified with reference numeral 210 in FIG. 1 are electrically coupled to the pacemaker 220 and extend into the patient's heart 116 via a vein 118. Disposed generally near a distal end of the sensors 210 are one or more exposed conductive electrodes for receiving electrical cardiac signals or delivering electrical pacing stimuli to the heart 116. The sensors 210 may be implanted with their distal end situated in either the atrium or ventricle of the heart 116. In an alternative embodiment, the sensors 210, or the leads associated with the sensors 210, may be situated in a blood vessel on the heart 116, such a save in 118.

Figure 2:
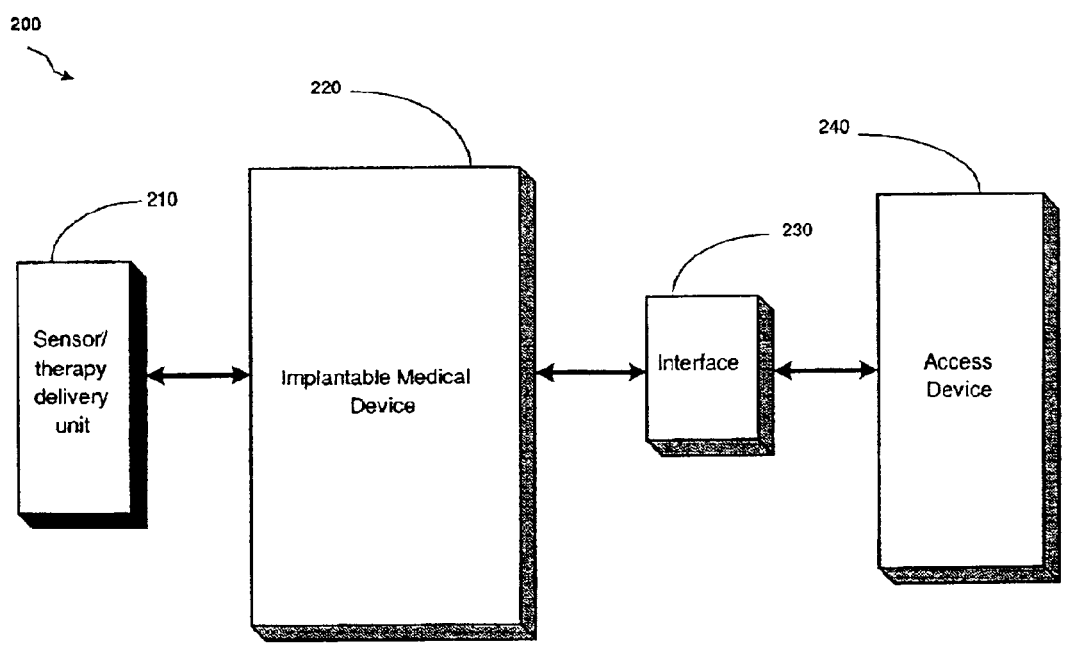
FIG. 2 illustrates a simplified block diagram representation of an implantable medical device system in accordance with one illustrative embodiment of the present invention.

Turning now to FIG. 2, a system 200, in accordance with one embodiment of the present invention, is illustrated. The system 200 comprises a sensor 210, an implantable medical device 220, an access device 240, and an interface 230 that provides a communication link between the implantable medical device 220 and the access device 240. Embodiments of the present invention provide a plurality of physiological data from the sensor 210, which are then processed and stored. The access device 240 can then be used to monitor and analyze the organized data from the implantable medical device via the interface 230.

Figure 3:
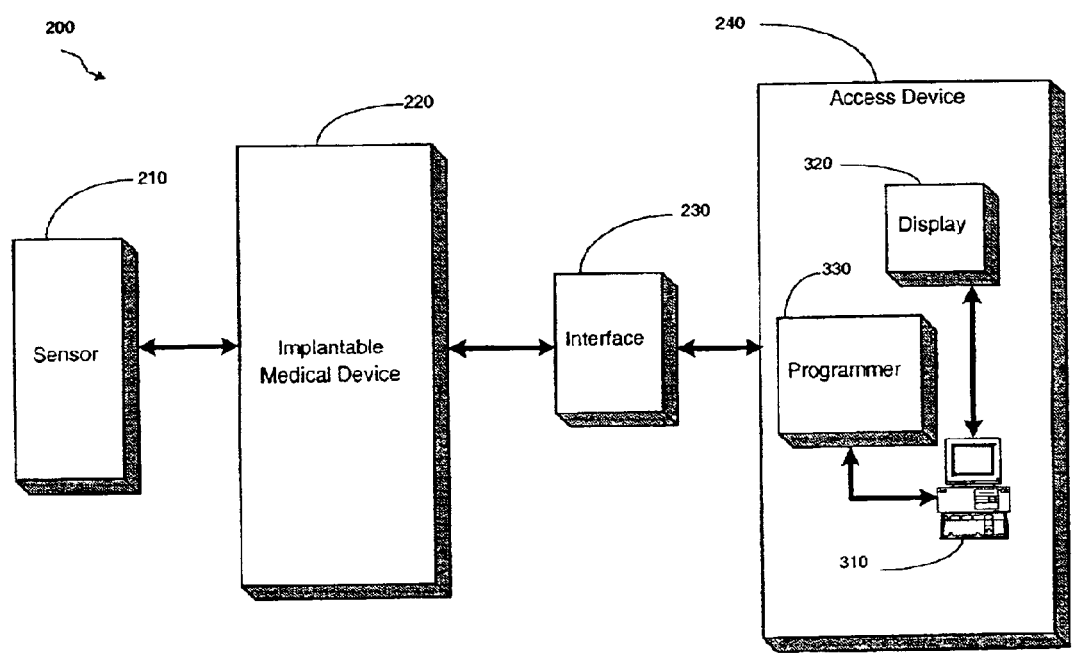
FIG. 3 illustrates a more detailed block diagram representation of an access device of FIG. 2, in accordance with one illustrative embodiment of the present invention.

Turning now to FIG. 3, a more detailed illustration of the access device 240 is illustrated. In one embodiment, the access device 240 comprises a computer system 310, a display device 320, and a programmer 330. In one embodiment, the programmer 330 can be integrated into the computer system 310. The computer system 310 can prompt the acquisition of physiological data from the implantable medical device 220 via the interface 230. The computer system 310 can then display the physiological data on the display device 320. The display device 320 can display physiological data from the reference point of different time periods, different activity results, and the like. Generally, the interface 230 is a telemetry interface that is capable of facilitating two-way communications between the access device 240 and the implantable medical device 220. In one embodiment, the interface 230 provides wireless telemetry between the access device 240 and the implantable medical device 220. A number of processes can be used for telemetry communications that are known by those skilled in the art having benefit of the present disclosure.

Figure 4:
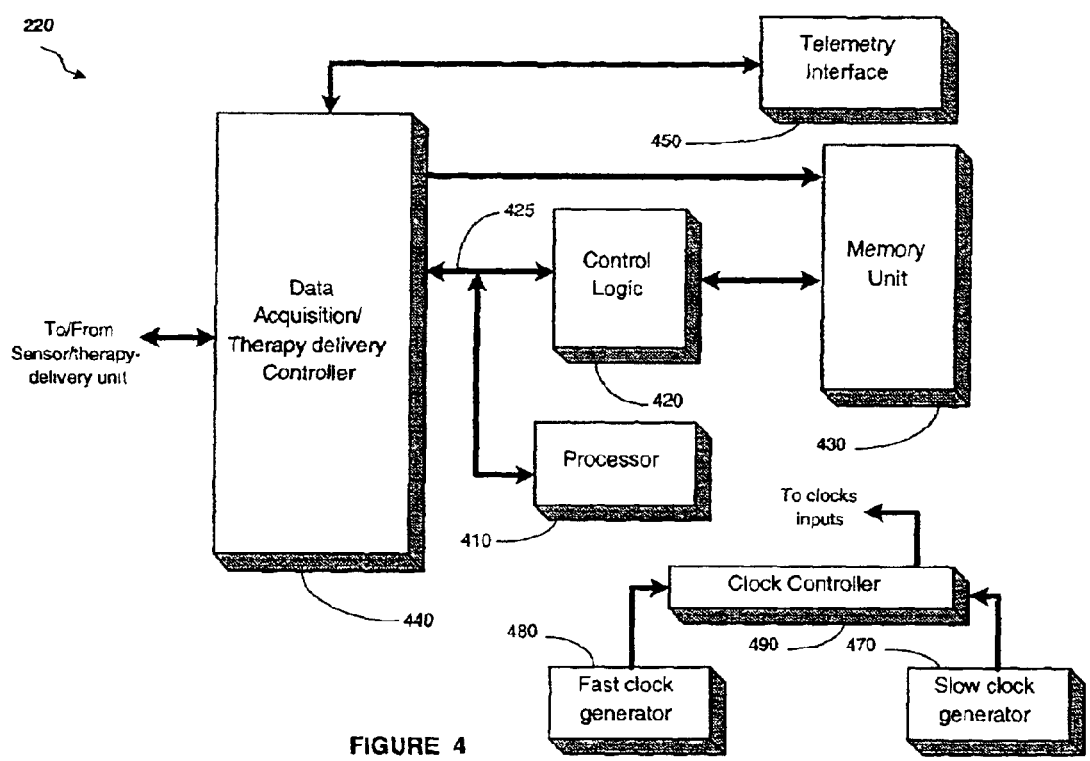
FIG. 4 illustrates a more detailed block diagram representation of an implantable medical device of FIG. 2, in accordance with one illustrative embodiment of the present invention.

Turning now to FIG. 4, a more detailed block diagram depiction of one embodiment of the implantable medical device 220 is illustrated. The implantable medical device 220 comprises a processor 410, a control logic 420, a memory unit 430, a data acquisition controller 440, a telemetry interface 450, a slow clock generator 470, a fast clock generator 480, and a clock controller 490. The processor 410 controls the operation of the implantable medical device 220. The processor 410 utilizes the control logic 420 to perform a plurality of operations, including memory access and storage operations, physiological data processing, and therapy deliver operations. The processor 410 communicates with the control logic 420 and the data acquisition controller 440 via a bus line 425. The control logic 420 sends control signals to the memory unit 430 for controlling memory 430, and to the data acquisition controller 440, which controls the acquisition of physiological data and drives output signals to the telemetry interface 450.

The telemetry interface 450 can facilitate real-time access of physiological data acquired by the data acquisition controller 440. Therefore, a physician can view physiological data on a real time basis by accessing the data acquisition controller 440, via the telemetry interface 450. The data acquisition controller 440 can retrieve physiological data, process such data, and deliver physiological data to the data acquisition controller 440.

In one embodiment, the implantable medical device 220 invokes a slow clock generator 470 to enter a slow-clock mode (slow-clock domain), which utilizes less power. For example, the slow clock generator 470 may produce a clock of a frequency of approximately 32 kHz. The implantable medical device 220 may invoke the operation of the fast clock generator 480 to enter a fast-clock mode (fast-clock domain). For example, the fast clock generator 480 may generate a clock of a frequency of approximately 2.8 MHz. In one embodiment, the fast-clock mode is invoked when a physiological event (e.g., a cardiac event) is detected. In the fast-clock mode, all operations of the implantable medical device 220, such as physiological data processing and therapy delivery functions, are generally active. Furthermore, the fast-clock mode may be invoked at predetermined intervals (e.g., once every 1000 milliseconds) to perform diagnostics operations, such as memory refreshing, lead diagnostics, battery measurements, and the like. In one embodiment, the transition from a slow clock domain to a fast clock domain comprises changing the circuit operation from a slow clock operating frequency to a fast clock operating frequency during a non-transition period of the slow clock.

One reason for clock synchronization is that one or more signals may pass between the slow clock domain and the fast clock domain. Furthermore, in one embodiment, the use of the fast clock may be delayed until the slow clock is synchronized with the fast clock. Therefore, the initial operation performed by the implatable medical device 220 in the fast clock mode would be in synchronized with the operation of the device 220 in the slow clock mode. The overall stability of the circuitry in the implantable medical device 220 may be more stabilized by employing the synchronization of clock domains.

The clock controller 490 in the implantable medical device 220 controls at which frequency the circuitry in the implantable medical device 220 operates. Generally, the fast clock generator 480 is used to operate the processor 410 and certain circuits, such as the memory unit 430, in the implantable medical device 220. The slow clock generator 470 provides the clock signal for the operation of certain circuitry in the implantable medical device 220, such as the data acquisition controller 440. During certain conditions, the slow clock generator 470 provides the operational clock signals for the implantable medical device 220. Under circumstances such as a cardiac event or certain predetermined diagnostic time frames, the fast clock generator 480 is invoked by the clock controller 490. The slow clock is used for certain operations to conserve power utilized by the implantable medical device 220.

Figure 5:
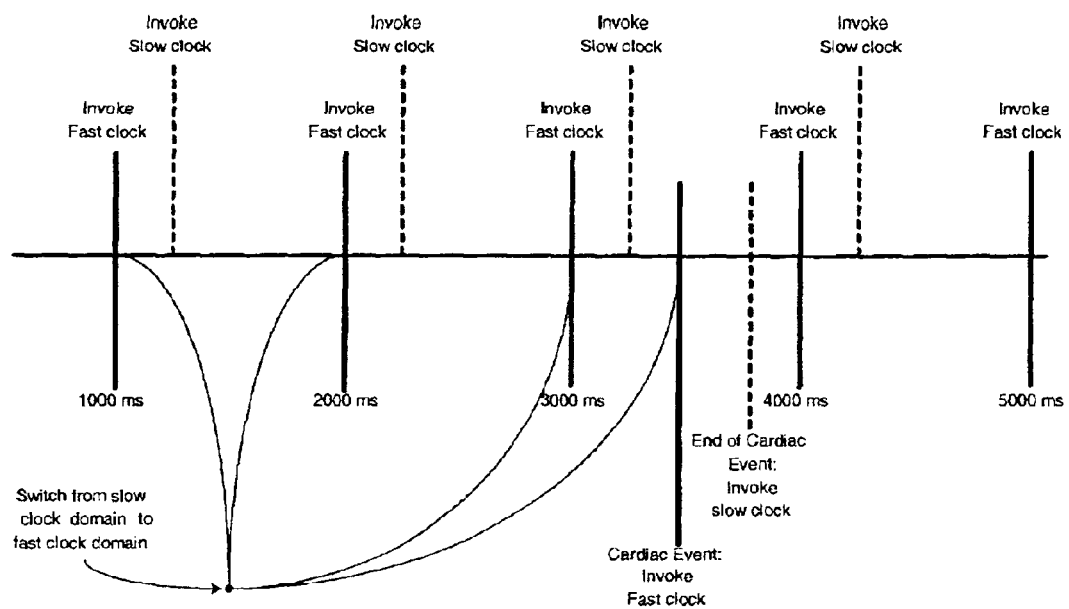
FIG. 5 illustrates a time-line diagram of a clock switching function in accordance with one embodiment of the present invention.

Turning now to FIG. 5, a timing diagram illustrating a sample of events that show the slow clock and the fast clock transitions, in accordance with one embodiment of the present invention is illustrated. As indicated in FIG. 5, approximately one-second intervals (1000 millisecond), the fast clock generator 480 is invoked. This is done to perform certain circuit diagnostic functions. These diagnostic functions include performing a memory refresh task, a logging of certain status signals into memory, checking impedance and other electrical characteristics of the lead 210, common battery measurements, and the like. In the interim, the operation of the implantable medical device 220 is performed using the slow clock, from the slow clock generator 470.

As shown in the example of FIG. 5, the implantable medical device 220 operates at a slow clock frequency until the 1000 millisecond mark, then the fast clock is initiated. After performing certain diagnostics, the fast clock is stopped and the slow clock is operational. Subsequently, the fast clock generator is invoked again at the 2,000 millisecond mark, and the 3,000 millisecond mark, and so on. Upon detection of a cardiac event by the implantable medical device 220, the fast clock is immediately invoked, wherein the implantable medical device 220 is fully operational.

As illustrated in FIG. 5, after the 3,000 millisecond mark, the implantable medical device 220 operates at a slow clock frequency until the cardiac event is detected. Once the response to the cardiac event has been performed, the implantable medical device 220 again invokes the slow clock for conservation of energy. Subsequently, at the 4,000 and the 5,000 millisecond marks, the operation of the slow clock is replaced by the fast clock to perform diagnostics. The switching between the fast and the slow clocks can cause jitters, unintended rising edge in certain digital signals, among other errors. Embodiments of the present invention reduce the possibility of the aforementioned errors during the switching from the slow clock to the fast clock and vice versa.

Figure 6:
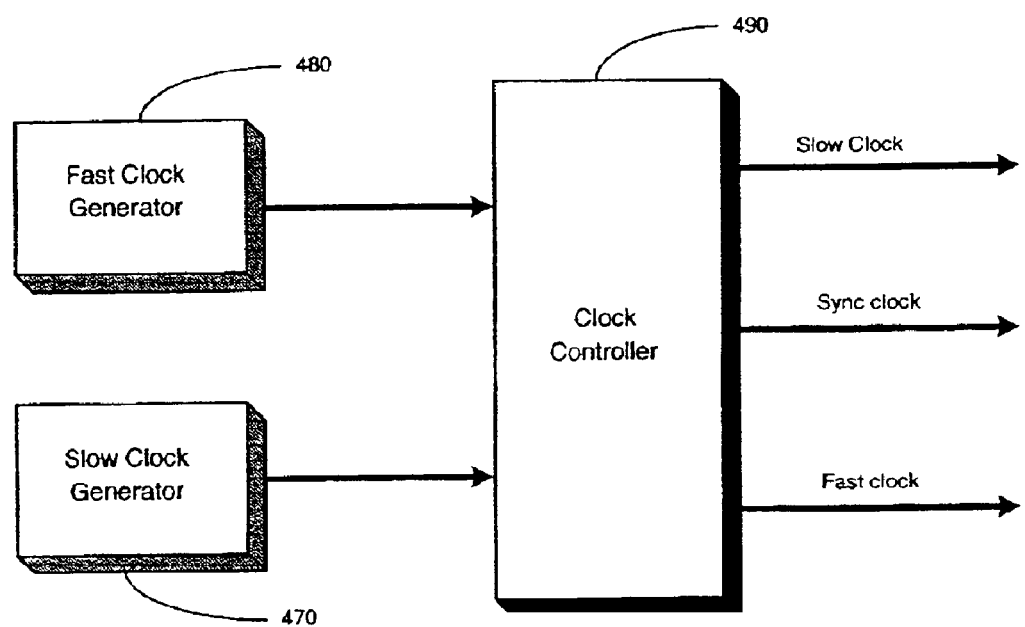
FIG. 6 illustrates a block diagram representation of the operation of a clock controller of FIG. 4, in accordance with one illustrative embodiment of the present invention.

Turning now to FIG. 6, a block diagram representation of an interaction between the fast clock generator 480, the slow clock generator 470, and the clock controller 490 is illustrated. Clock frequency signals generated by the fast clock generator 480 and the slow clock generator 470 are sent to the clock controller 490. The clock controller 490 controls the switching of certain digital signals that control the clock operations of other circuitry in the implantable medical device 220. The clock controller 490 provides a slow clock, and a slow sync clock, and a fast clock. In an alternative embodiment, the slow sync clock and the slow clock are generally on one signal line. A more detailed representation of the clock controller 490 is provided in FIG. 7.

Figure 7:
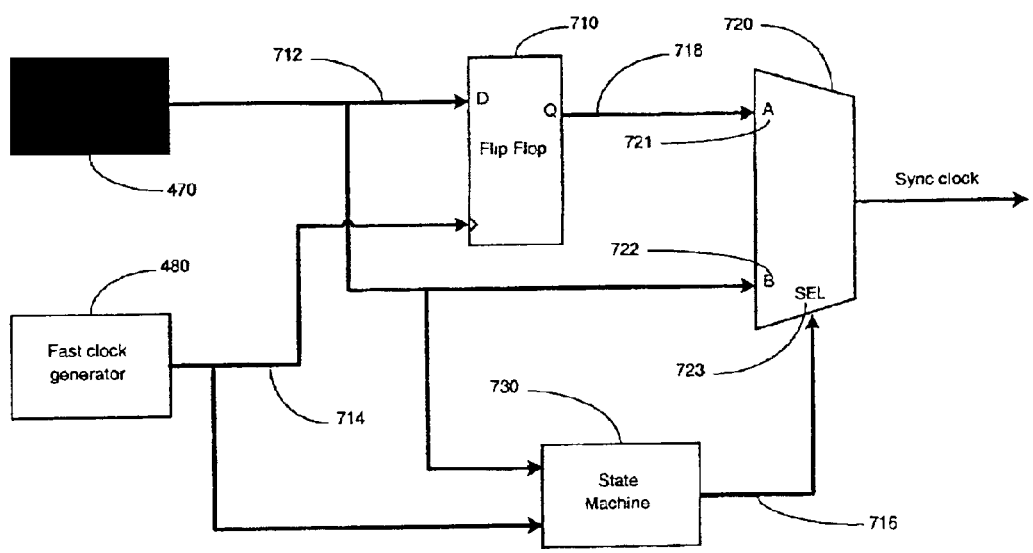
FIG. 7 illustrates a block diagram representation of the clock controller of FIG. 4, in accordance with one illustrative embodiment of the present invention.

Turning now to FIG. 7, the clock controller 490 comprises a D-flip-flop 710, a multiplexer 720, and a state machine 730 that performs a transition from the slow clock operation to the fast clock operation. The slow clock generator 470 provides a slow clock signal (e.g., 32 KHz signal) to the D-flip-flop 710 on a line 712. The D-flip-flop is also clocked by the fast clock generator 480 on a line 714. The D-flip-flop 710 is then used to clock the slow clock signal from the line 712 onto the output of the D-flip-flop 710 on the line 718.

The output of the D-flip-flop on the line 718 comprises a synced slow clock, which is synced (e.g., the rising and falling edge of the slow clock being synced to the rising edge of the fast clock) to the fast clock, therefore reducing any jitters or other errors on a transition. The synced slow clock is then sent to the A input 721 of a multiplexer 720. The B input 722 to the multiplexer 720 is a signal directly from the slow clock generator 470, which is not synced. A select signal on the line 716 is sent to the multiplexer 720 into its select input 723, from the state machine 740 for selection between the non-synced slow clock and the synced slow clock. Switching from the slow clock to the synced slow clock is timed by the state machine 730 to coincide with invoking the processor 410 in the implantable medical device 220.

Figure 8A:
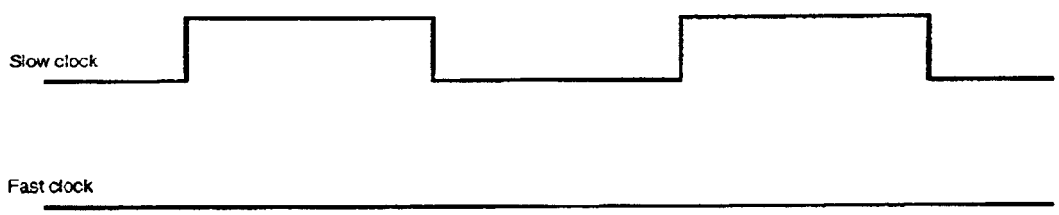
FIGS. 8a and 8b illustrate a timing diagram relating to synchronization of clock domains, in accordance with one illustrative embodiment of the present invention.
Figure 8B:
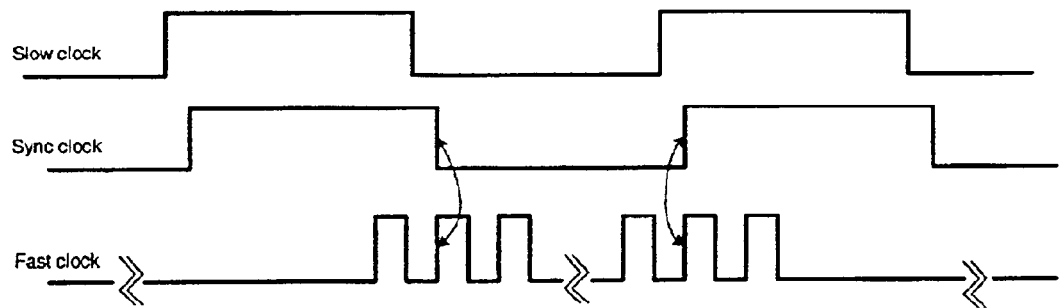

Turning now to FIG. 8A, a timing diagram that shows the operation of the implantable medical device 220 during a normal power-saving mode, is illustrated. During the normal power saving mode operation of the implantable medical device 220 the slow clock is used for the operation and the fast clock line is a straight line (i.e., fast clock is not generated), indicating the fast clock does not exist at this time. During certain time frames described above, or upon detecting a cardiac event, the implantable medical device 220 invokes the fast clock, where the processor and other peripheral devices are fully active in the implantable medical device 220. As indicated in FIG. 8B, the timing of the synced clock is slightly different from the timing of the slow clock. However, the fast clock (e.g., the rising edge of the fast clock) is in sync with the rising and falling edge of the slow clock. Therefore, the probability of glitches and other errors during the invocation of the fast clock is reduced.

Figure 9:
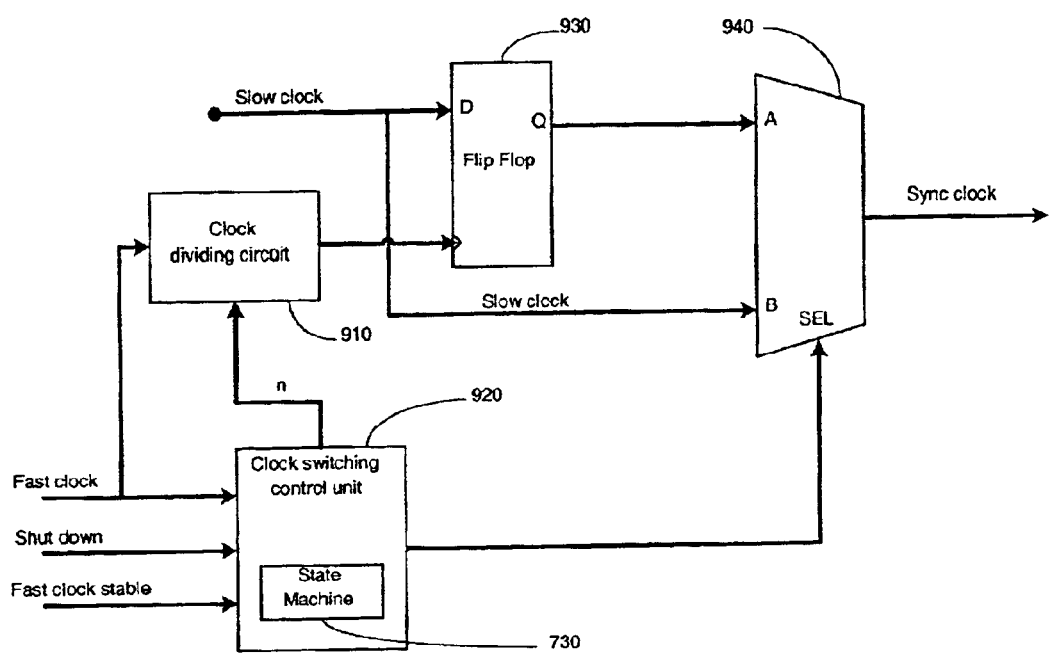
FIG. 9 illustrates a block diagram representation of performing a clock-mode switching, in accordance with one illustrative embodiment of the present invention.

The implantable medical device 220 may comprise components that operate at a plurality of frequencies that are multiples, or fractions, of the fast clock. Turning now to FIG. 9, a circuit for providing a synced clock that has a fraction of the frequency of the fast clock, is illustrated. The fast clock is divided by a clock dividing circuit 910, which divides the fast clock by a value n. The value used to divide the clock dividing circuit is provided by the clock switching control unit 920, which may comprise the state machine 730. The output of the clock dividing circuit is used to clock the slow clock through a flip-flop 930 onto a multiplexer 940. Another input into the multiplexer 940 is slow clock. The clock switching control unit 920 selects between the slow clock and the synced, divided clock for operation of certain components in the implantable medical device 220. Therefore, a plurality of clock signals that are synced can operate a plurality of components in the implantable medical device 220.

Figure 10:
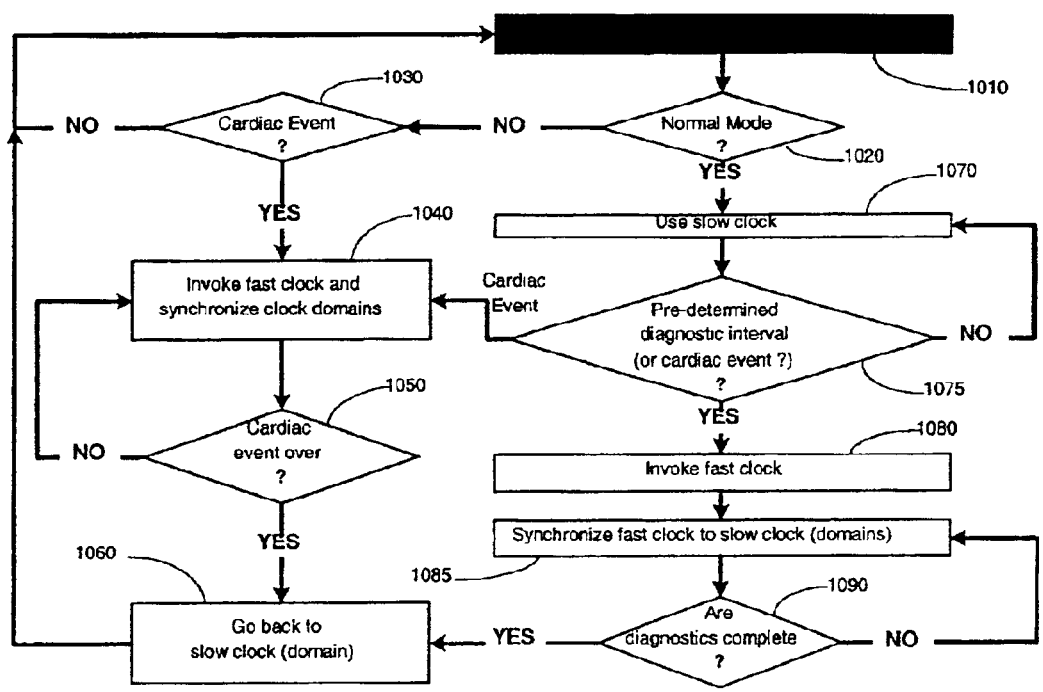
FIG. 10 illustrates a flowchart depiction of the method in accordance with illustrative one embodiment of the present invention.

Turning now to FIG. 10, a flowchart depiction of the method in accordance with one embodiment of the present invention is illustrated. The system 200 determines a mode of operation for the operation of the implantable medical device 220 (block 1010). In other words, the mode of operation may be a normal power save mode wherein certain components such as a processor are in a low power mode, where the slow clock is used for the operation. Another mode may be one that is initiated by the operation of the fast clock in which all components in the implantable medical device 220 are invoked. Such a mode may be invoked by a predetermined diagnostic period, such as every 1,000 millisecond or by the detection of a cardiac event in which a therapy response may be required.

The implantable medical device 220 determines whether a normal mode is to be invoked (block 1020). When the implantable medical device 220 determines that a normal mode is not invoked, the device 220 determines whether there is a cardiac event (block 1030). When the device 220 determines that there is no cardiac event, the device 220 again checks to determine which mode of operation is to be invoked. When the implantable medical device 220 determines that a cardiac event has occurred (block 1030), the device 220 invokes the fast clock and the slow clock and fast clock domains are synchronized (block 1040). Until the cardiac event is terminated and/or all responses to the cardiac event are completed, the fast clock is invoked such that all components in the implantable medical device 220 are operational at full capacity (see the loop from blocks 1050 to 1040 back to 1050). When the cardiac event is over, the implantable medical device 220 places the operation of the device 220 into a slow clock mode (block 1060). At any given point, when a cardiac event is detected, the implantable medical device 220 is placed into a fast clock mode.

Referring to block 1020, when the device 220 determines that a normal mode is to be maintained, the slow clock is invoked (block 1070). During the operation of the slow clock mode, the device 220 checks to determine whether a predetermined diagnostic interval has occurred (block 1075). Furthermore, the device 220 checks to determine whether a cardiac event has occurred. When the implantable medical device 220 determines that a predetermined diagnostic time period has not occurred, the use of the slow clock is maintained. When the device 220 determines that a cardiac event has occurred, clock domains are changed as described above (see path from block 1075 to 1040). When the device 220 determines that a predetermined diagnostic time interval has been reached, the fast clock is invoked (block 1080). Subsequently, the device 220 syncs the fast clock to the slow clock (1085).

The implantable medical device 220 then determines whether the diagnostic process is complete as indicated by firmware in the implantable medical device 220 (block 1090). When the diagnostic process is complete, the device 220 again goes back to the slow clock operation (the path from block 1090 to block 1060). When the implantable medical device 220 determines that the diagnostic period is not over, the operation of the fast clock is maintained. The end of the diagnostic process for the slow clock is once again maintained and is generally programmed into firmware placed in the implantable medical device 220.

Figure 11:
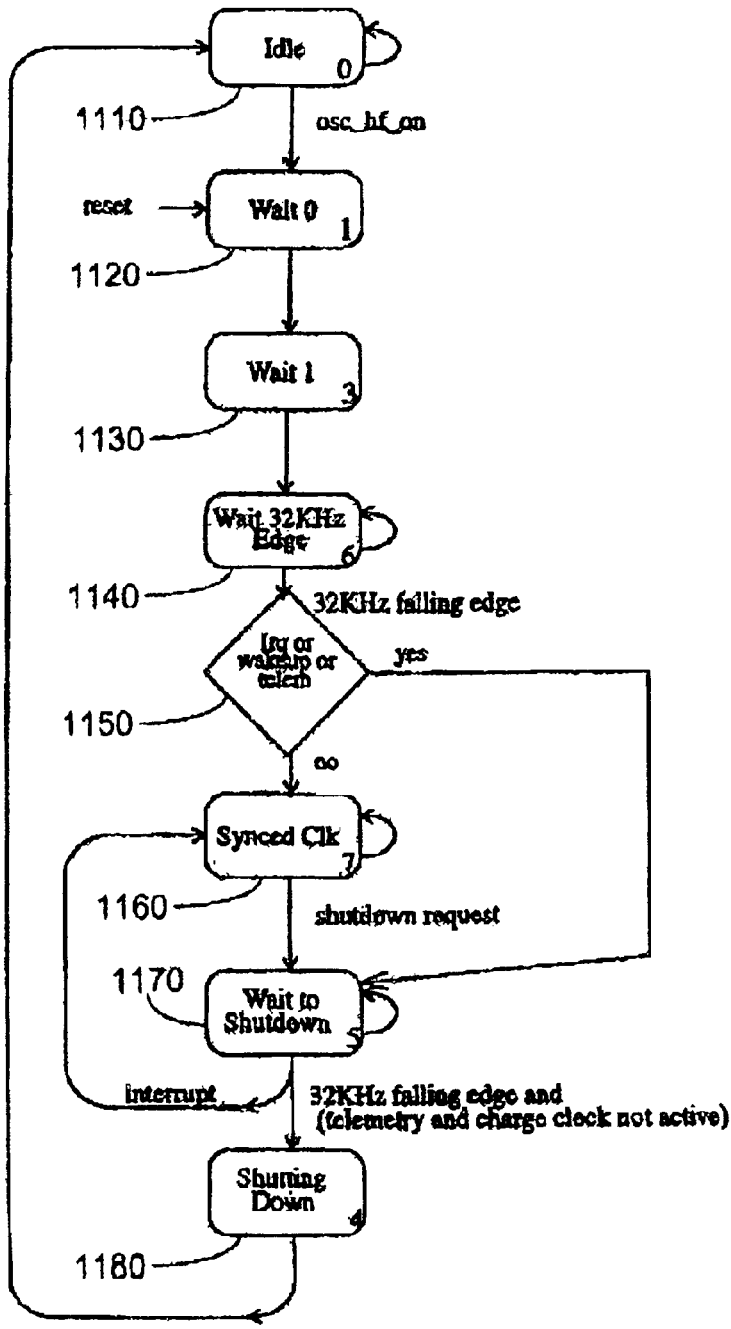
FIG. 11 illustrates a simplified depiction of a state machine in accordance with one illustrative embodiment of the present invention.

The operation described in FIG. 10, in one embodiment, can be performed by a state machine 730. One example of such a state machine 730, in accordance with one embodiment of the present invention, is illustrated in FIG. 11. The initial state of the state machine 730 is an idle state (state 1110), until the insertion of the "signal oscillator high frequency on" signal (osc_hf_on), which invokes the high frequency clock. The operation of the high frequency clock is invoked in the state 1120 and 1130, which are wait states. The wait state 0 has an input of a reset signal, which brings the state machine 730 to state 1120. The state 1140 is a wait state until the edge of a slow clock signal (e.g., 32 kHz edge) is realized.

On the falling edge of the low frequency signal (e.g., 32 kHz signal), the assertion of an interrupt request, a wake up request, or a telemetry request is checked. If an interrupt request, a wake up request, or a telemetry request is detected, the state machine 730 jumps to the state 1170. If no such request is detected, the slow clock is synced (state 1160). The state 1160 is maintained until a shutdown request is received. The state machine 730 then moves to the state 1170, where a wait to shut down state is maintained. When an interrupt is received, the clock is synced (the state machine moves from state 1170 to 1160). When a telemetry and charge clock to charge the capacitor in the device 220 are not active upon the falling edge of the 32 KHz signal, the shutting down state (state 1180) is reached, which then goes into the idle state 1110, awaiting the osc_hf_on signal. Alternative embodiments of the implantation of the state machine 730 can be utilized and remain within the spirit of the present invention.

Figure 12:
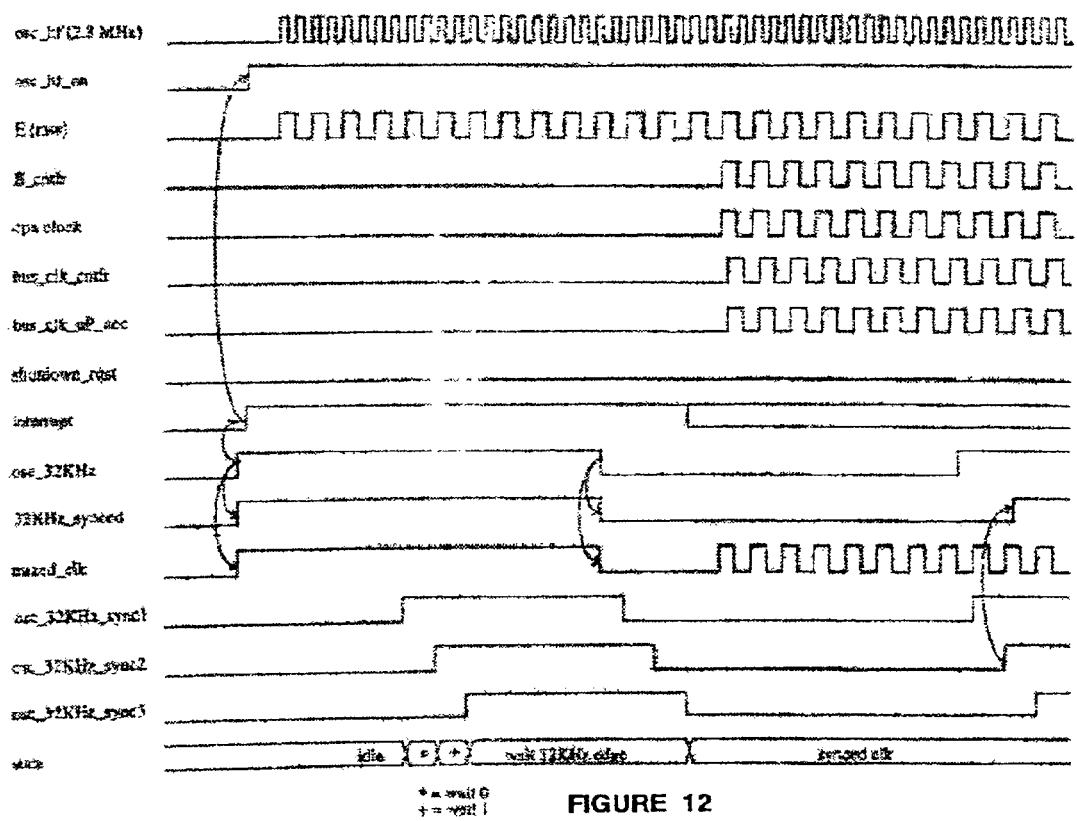
FIG. 12 illustrates a timing diagram relating to the state machine of FIG. 11, in accordance with one illustrative embodiment of the present invention; and Appendix A provides an example of implementing a hardware descriptive language to provide the synchronization of clock domains, in accordance with one embodiment of the present invention.

A timing diagram in relation to the state machine described in FIG. 11 is provided in FIG. 12. The timing diagram illustrated in FIG. 12 tracks the operation of the state machine 730, as described above. Furthermore, Appendix A provides one method of invoking the state machine 730 using hardware descriptive language (HDL), as provided. Those skilled in the art, having the benefit of the present disclosure, can implement the state machine 730 described above by referring to the hardware descriptive language (HDL) provided in Appendix A. The switching of the clock frequencies and the synchronizing of the clock domains described by the present invention can be utilized in a variety of electrical circuits including medical devices, commercial devices, computing devices, and the like.

The above detailed description is an illustrative example of an embodiment in accordance with the present invention, of the implementation of the implantable medical device 220 described above. It should be appreciated that other implementations and/or embodiments can be employed within the spirit of the present invention. The teachings of the present invention can be utilized for a variety of systems relating to data acquisition, data storage, or presentation of data.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. An implantable medical device, comprising:
    means to acquire physiological data of a patient;
    means to deliver therapy to a patient based upon acquired physiological data;
    a slow clock signal generator providing a slow clock signal;
    a fast clock signal generator providing a fast clock signal;
    a clock controller coupled to said slow clock signal generator and to said fast clock signal generator, said clock controller providing a synchronized slow clock signal synchronized with a fast clock signal by latching a state of the slow clock signal upon each occurrence of a predetermined transition of the fast clock signal and providing the fast clock signal;
    a processor controlling operations of the therapy delivery means; and
    a control logic circuit operatively coupled to said processor and generating a control signal in response to a command from said processor to cause the clock controller to selectively apply the synchronized slow clock signal and the fast clock signal to a clock driven circuit in the therapy delivery means.

2. The implantable medical device of claim 1, wherein the processor sends a command to the control logic circuit to apply the synchronized slow clock signal when patient circumstances permit a low power operation of he therapy delivery means.

3. The implantable medical device of claim 2, wherein the processor sends a command to the control logic circuit to apply the fast clock signal when patient circumstances require a normal operation of the therapy delivery means.

4. The implantable medical device of claim 1, wherein the processor executes a program of instructions to provide a power save mode of operation of the therapy delivery means and the processor that invokes use of the synchronized slow clock signal and to provide a fully operational mode of operation of the therapy delivery means and the processor in response to a patient event that invokes use of the fast clock signal.

5. The implantable medical device of claim 1, wherein the fast clock generator produces a fast clock signal at a predetermined frequency and the clock controller includes a clock dividing circuit coupled to the fast clock generator to provide a clock signal that is a fraction of the frequency of the fast clock signal.

6. The implantable medical device of claim 1, wherein the means to acquire physiological data of a patient, the means to deliver therapy to a patient based upon acquired physiological data, and the processor implement a cardiac pacemaker.

7. The implantable medical device of claim 6, wherein the processor executes a program of instructions to provide a power save mode of operation of the therapy delivery means and the processor that invokes use of the synchronized slow clock signal and to provide a fully operational mode of operation of the therapy delivery means and the processor in response to a patient cardiac event that invokes use of the fast clock signal.

* * * * *

UNITED STATES PATENT AND TRADEMARK OFFICE
CERTIFICATE OF CORRECTION

PATENT NO. : 6,988,215 B2
APPLICATION NO. : 09/952914
DATED : January 17, 2006
INVENTOR(S) : Vincent E. Splett et al.

It is certified that error appears in the above-identified patent and that said Letters Patent is hereby corrected as shown below:

Claim 2, Col. 10, line 15, delete "of he therapy"

and insert in place thereof -- of the therapy --.

Signed and Sealed this

Twenty-fourth Day of February, 2009

JOHN DOLL
*Acting Director of the United States Patent and Trademark Office*